(12) United States Patent
Hoffman et al.

(10) Patent No.: US 7,985,194 B2
(45) Date of Patent: Jul. 26, 2011

(54) PATELLA ALIGNMENT DEVICE

(76) Inventors: Maxine Hoffman, Dayton, OH (US);
Philip Doepker, Dayton, OH (US);
Austin Mitchell, Pittsburgh, PA (US);
Jessica Marie Northridge, Xenia, OH (US); Daniel James Petit, Wooster, OH (US)

( * ) Notice: Subject to any disclaimer, the term of this patent is extended or adjusted under 35 U.S.C. 154(b) by 0 days.

(21) Appl. No.: 12/944,613

(22) Filed: Nov. 11, 2010

(65) Prior Publication Data

US 2011/0112454 A1  May 12, 2011

Related U.S. Application Data

(60) Provisional application No. 61/260,679, filed on Nov. 12, 2009.

(51) Int. Cl.
*A61F 5/00* (2006.01)
*A61F 5/30* (2006.01)
*A41D 13/00* (2006.01)

(52) U.S. Cl. .............. 602/26; 2/22; 128/112.1

(58) Field of Classification Search .............. 602/61–63, 602/27, 26, 20, 206, 75, 53, 60, 5, 6, 8; 2/22, 2/24, 62; 128/882, 112.1, 113.1, 114.1, 121.1
See application file for complete search history.

(56) References Cited

U.S. PATENT DOCUMENTS

| 5,865,782 | A | * | 2/1999 | Fareed | .............. 602/62 |
| 7,361,154 | B2 | | 4/2008 | Jablonka | |
| 2004/0153017 | A1 | * | 8/2004 | Simmons et al. | .............. 602/26 |

OTHER PUBLICATIONS www.futuro-usa.com, Futuro Adjustable Knee Strap, website.
www.supports4less.com, Knee Patella Support by Alex Orthopedic, website.
www.supports4less.com, McDavid 414 Jumper's Knee Strap, website.
www.supports4less.com, Cramer Patella Tendon Strap, website.
www.supports4less.com, Hely Weber Matt Knee Patellar Strap, website.
www.kneeshop.com, Cho-Pat's Dual Action Knee Strap, website.
www.kneeshop.com, Cho Pat's Counter-Force Knee Wrap, website.
www.kneeshop.com, Cho-Pat's I.T.B. strap, website.
www.kneeshop.com, KneedIt Therapeutic Knee Guard, website.
www.kneeshop.com, The Bioskin Q Baby, website.
www.kneeshop.com, The Pro-Tec Patellar Tendon Strap, website.
www.kneeshop.com, AirCast infrapatellar knee band, website.
www.Sammonspreston.com, Sport-Trac Knee Strap, website.
www.sammonspreston.com, Tendon Trak, website.
www.sammonspreston.com, Fabrifoam PattStrap Knee Strap, website.
www.sammonspreston.com, Gel Band Patella Strap, website.
www.sammonspreston.com, Mueller Jumper's Knee Strap, website.
www.supportsusa.com, Bio Skin Q-Baby Patella Tendon Strap, website.

* cited by examiner

*Primary Examiner* — Patricia Bianco
*Assistant Examiner* — Tarla Patel
(74) *Attorney, Agent, or Firm* — Darin Barber; Sam S. Han

(57) ABSTRACT

One embodiment of the invention is a knee (or elbow) band assembly 100 that has a pocket assembly 106 containing a flexible pad 200 with rounded surfaces 112b, 116b separated by a valley 114b. The band assembly 100 is applied to a leg below the knee or to an arm above the elbow to improve body alignment and function and to relieve pain. The rounded surfaces 112a, 116a apply pressure to the limb to aid in alignment of the patellar or triceps tendons and to activate pressure points on the skin to stimulate the release of tension in the body and to stimulate the body's natural self-curative abilities.

1 Claim, 7 Drawing Sheets

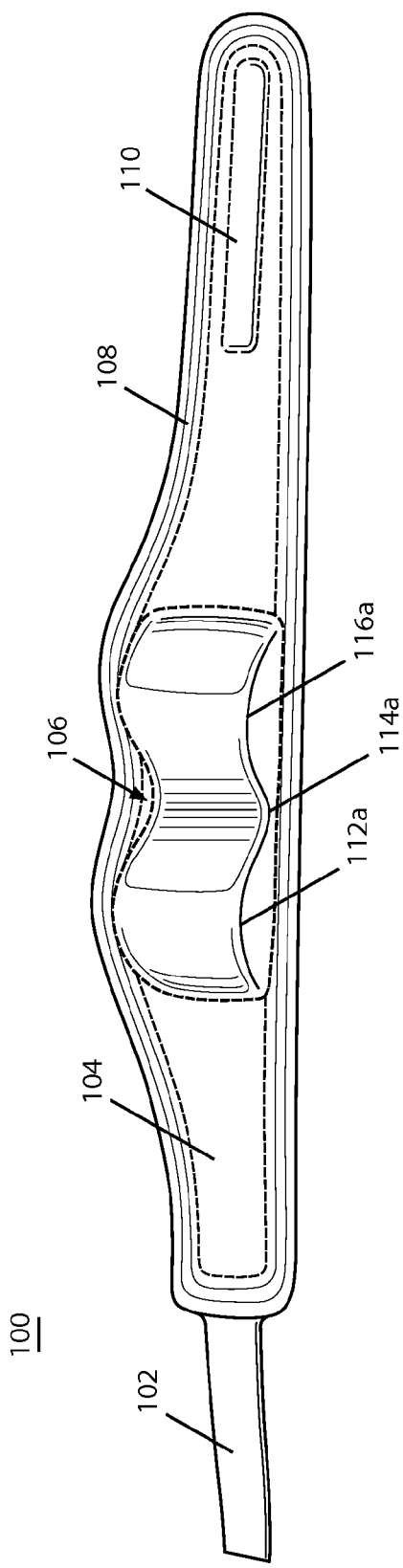
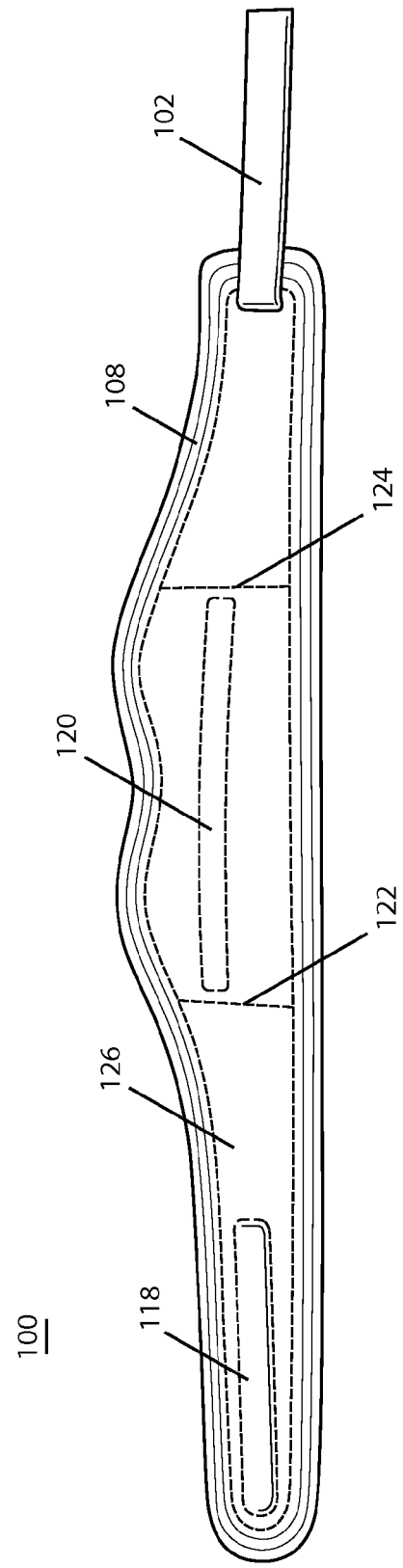
FIG.1A
FIG.1B

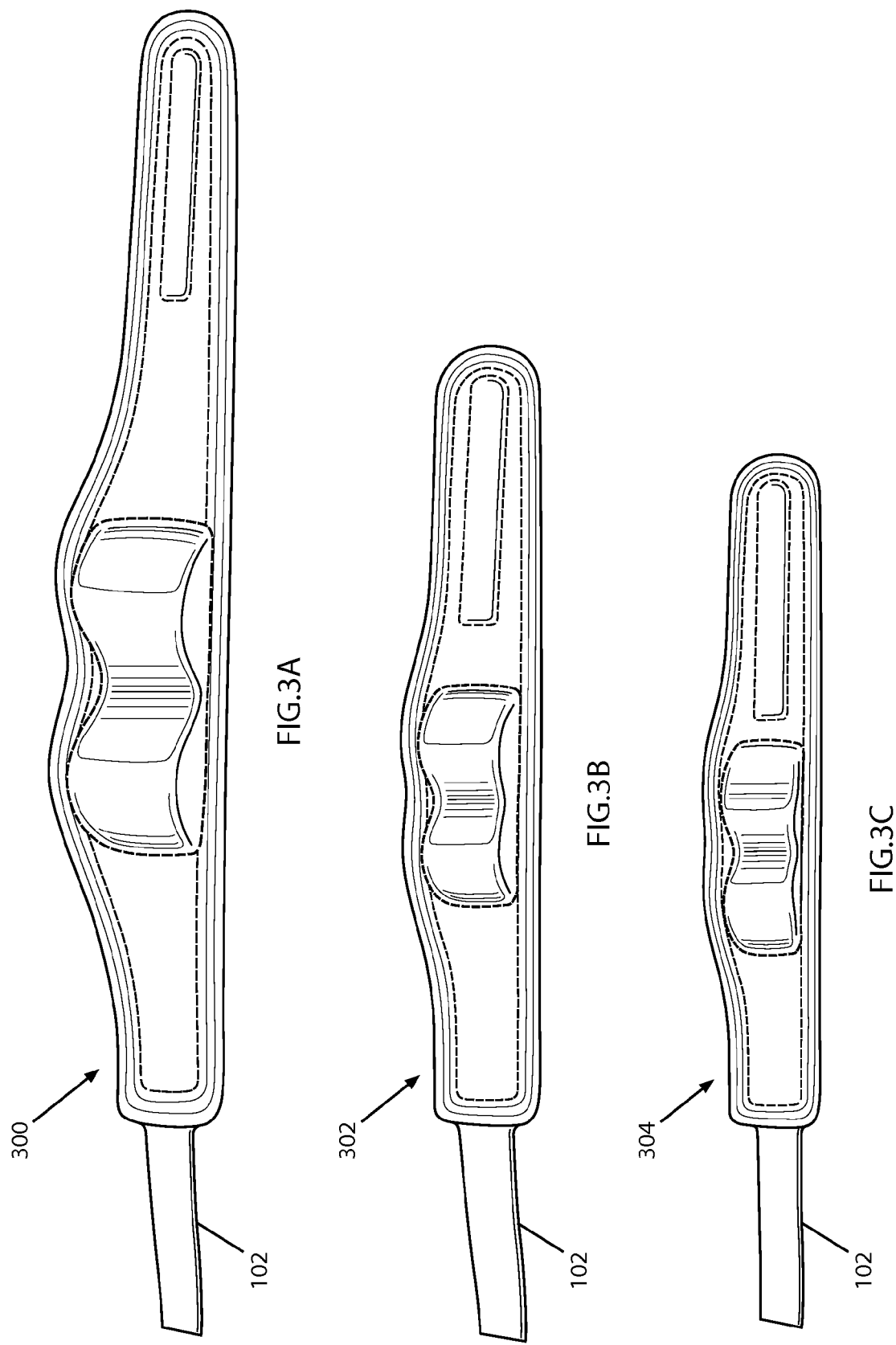

PATELLA ALIGNMENT DEVICE

CROSS-REFERENCE TO RELATED APPLICATIONS

This application claims the benefit of U.S. Provisional Application No. 61/260,679, filed Nov. 12, 2009, having the title "Patella Alignment Device," by Hoffman et al., which is incorporated herein by reference in its entirety.

FIELD OF DISCLOSURE

This disclosure relates to flexible bands that are applied to the knee or elbow area to relieve pain and to improve alignment and function of the body.

BACKGROUND

Currently-available braces produce a static compression around joints by applying pressure directly over a joint or tendon area. Usually, the compression provides decreased mobility in hopes of decreasing pain and future deterioration of the joint. But decreasing normal movement in one area of the body can create a negative influence on adjacent areas and areas more distant from the stabilized area.

Also, fixation of a particular joint can negatively impact elasticity and functionality of connective tissue. Such fixation can negatively impact the normal flow and alignment of the organ meridian systems.

Currently-available braces are often bulky, uncomfortable, and/or unattractive. Many times they do not come in adequate size ranges and/or are difficult to adjust. They often have stiff and inflexible areas that are uncomfortable.

Thus, an unaddressed need exists in the industry to address these deficiencies and inadequacies.

SUMMARY

One embodiment of the invention is a band assembly fabricated from flexible material and having a pocket assembly. Inside the pocket assembly is a flexible pad that has rounded surfaces separated by a valley. When the band assembly is properly positioned on the knee area of a human subject, these rounded surfaces align the patellar tendon with the trochlear groove.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Also, like reference numerals designate corresponding parts throughout the several views.

FIG. 1A is a front, perspective view of a band assembly.
FIG. 1B is a back, perspective view of the band assembly.
FIG. 3A is a front, perspective view of the band assembly in an adult size.
FIG. 3B is a front, perspective view of the band assembly in a child size.
FIG. 3C is a front, perspective view of the band assembly in an infant size.

DETAILED DESCRIPTION OF THE INVENTION

Figure 2A:
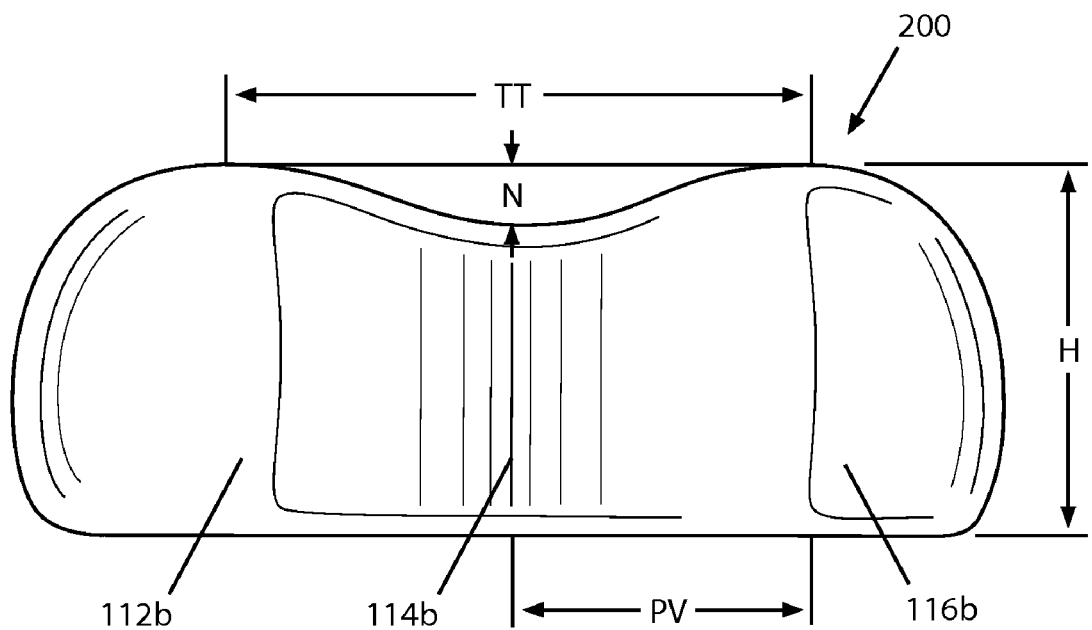
FIG. 2A is a front view of a flexible pad.

Reference is now made in detail to the description of the embodiments as illustrated in the drawings. While several embodiments are described in connection with these drawings, there is no intent to limit the disclosure to the embodiment or embodiments disclosed herein. On the contrary, the intent is to cover all alternatives, modifications, and equivalents.

The disclosed band assembly has many curative properties when properly applied to a human subject. When applied to a leg, the device applies firm, gentle pressure to the patellar tendon area and its surrounding tissue. The key is a flexible pad with rounded surfaces separated by a valley. When applied properly, a subject's patellar tendon resides in the valley while pressure from the rounded surfaces guides the tendon to correctly align with the subject's trochlear groove for improved muscle and joint function. A secondary effect of the pressure from the rounded surfaces is activation of acupressure points and release of tight connective tissue (fascia). This results in the patella (kneecap) moving to a more midline position. Other secondary effects are improved alignment throughout the body, pain reduction, and improved concentration and calming. All this is accomplished with the band assembly, which is comfortable to wear, is unobtrusive, and is non-restrictive, unlike previous devices that sought to align tendons by restricting their movement with pressure that was oftentimes uncomfortable and constrictive. As described in greater detail below, tests using the inventive band assembly show surprisingly superior results, as compared to other devices that are currently-available on the market.

Figure 4:
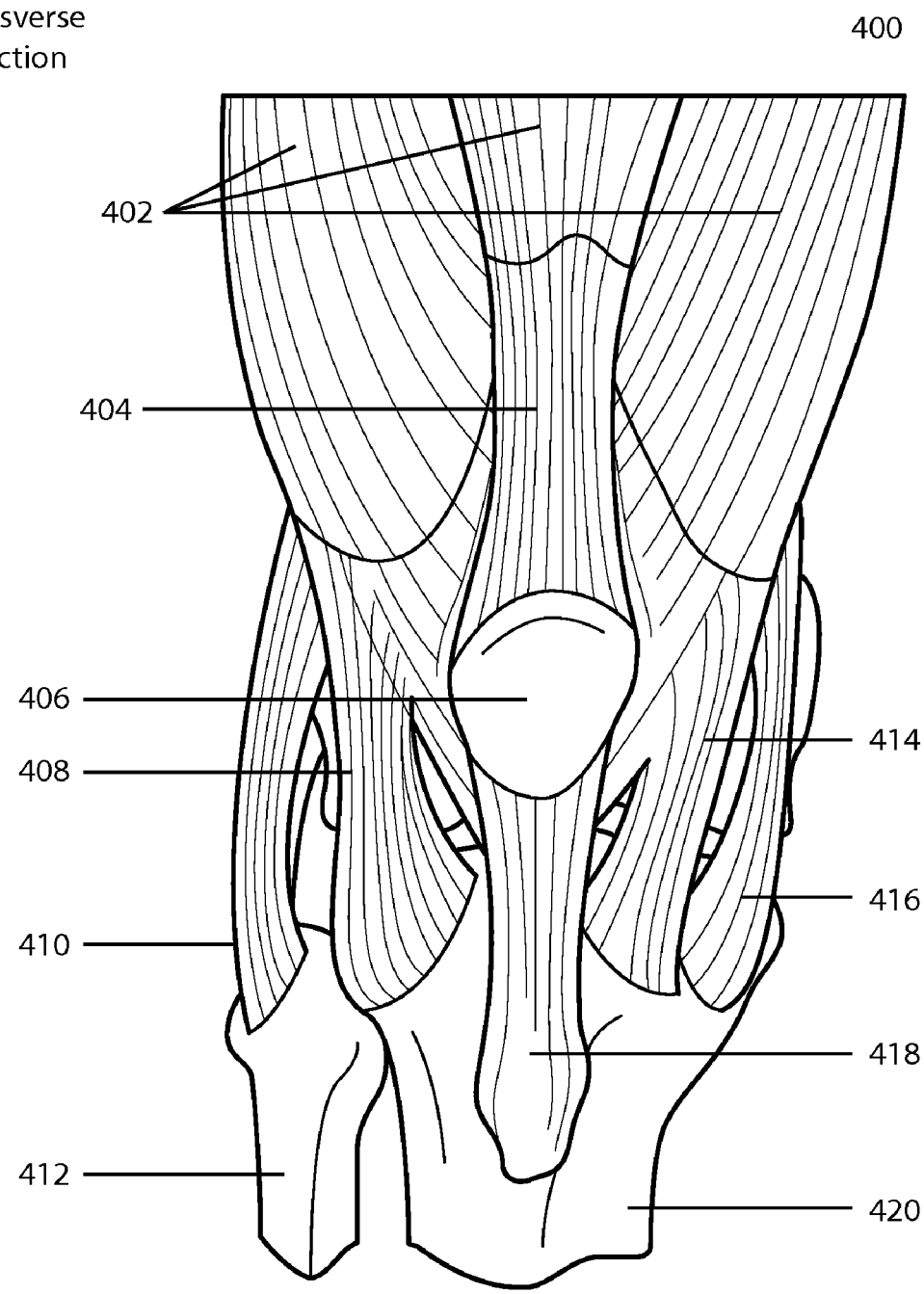
FIG. 4 is a drawing of a patellar tendon residing in the trochlear groove.

FIG. 1A and FIG. 1B show a band assembly 100. A VELCRO® hook fastener 102 is attached to the end of a flexible strap 126, which is made of neoprene or any other suitable material. A pocket assembly 106 is made by putting a flexible pad 200 (FIG. 2) inside a pocket that is formed by sewing the flexible strap 126 to a liner 104 and sewing 122, 124 it on both sides of the of the flexible pad 200. The liner 104 is made of polyester fabric with spandex to absorb sweat and prevent skin reactions in neoprene-sensitive persons. An elastic edging 108 surrounds the flexible strap 126 to help the strap maintain its shape and placement on a limb. A VELCRO® loop fastener 118 is sewn 110 to the flexible strap 126. Rounded ridges 112a, 116a of the pocket assembly 106 are the areas of the flexible strap 126 that exert gentle pressure on a leg on both sides of the patellar tendon 418 (FIG. 4). The patellar tendon 418 (FIG. 4) is surrounded by a valley 114a and is guided by pressure from the rounded ridges 112a, 116a, which serve to align the patellar tendon 418 (FIG. 4) with the trochlear groove. This pressure also influences connective tissue and acupressure points. A reinforcement strip 120 made of non-elastic twill tape is sewn on the inside of the flexible strap 126 to prevent stretching within that area of the flexible strap 126 and pocket assembly 106.

FIG. 2A is a front view of the flexible pad 200, which is straight on the bottom and has a rounded notch on the top. The notch is defined by a gap TT and an indentation N, and as described below a portion of the knee is cradled by this notch TT/N when the band assembly 100 is properly applied to a human knee. The rounded surfaces 112b, 116b run the direction and length of the flexible pad's height H and are separated by the valley 114b.

Figure 2B:
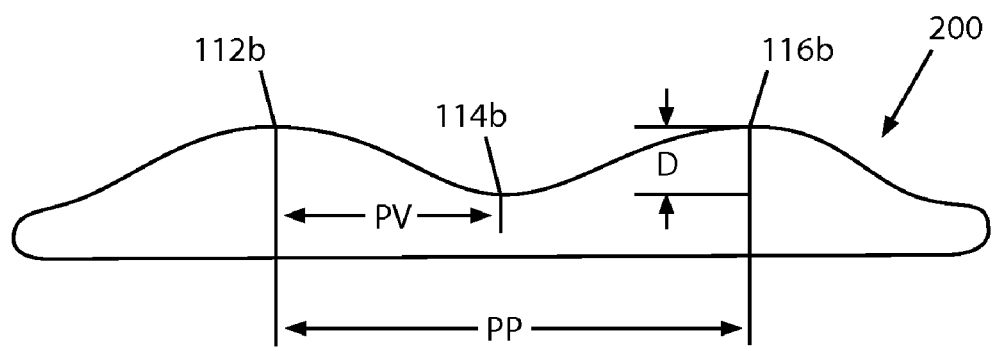
FIG. 2B is a bottom view of the flexible pad.

FIG. 2B is a bottom view of the flexible pad 200. In one embodiment, the flexible pad 200 is made of 10 lb.-flexible-urethane foam or other suitable material. When properly applied to a human subject, the patellar tendon 418 (FIG. 4) resides in the valley 114b and is aligned with the trochlear groove by pressure from the rounded surfaces 112b, 116b. Unlike other devices that are currently available on the market, the profile of the flexible pad 200, as seen from the bottom, is substantially curved. This curvature allows the rounded surfaces 112b, 116b to apply a distribution of pressure than cannot be realized with non-curved surfaces such as, for example, flat surfaces or square-step-function-like surfaces. This distribution, which results from the curvature and the firmness of the material, produces a better alignment, thereby resulting in superior results.

Patellar tendons can vary in width, length, and thickness throughout life. The average width of an infant patellar tendon is 0.51 inches, of a child patellar tendon is 0.59 inches, and of an adult patellar tendon is 1.06 inches. As shown in FIGS. 3A, 3B, and 3C, three different size flexible pads were made to accommodate tendons of various sizes for infants, children, and adults.

An adult-sized flexible pad measures approximately 2.2 inches from the peak of one rounded surface 112b to the peak of the other rounded surface 116b (peak-to-peak distance, labeled PP in FIG. 2B), with the lowest point in the valley 114b residing approximately mid-way between the peaks 112b, 116b (approximate mid-point distance labeled as PV in FIGS. 2A and 2B). The approximate distance from the peak height to the bottom of the valley 114b (depth, labeled D in FIG. 2B) is 0.25 inches. The height H is approximately 1.6 inches with a notch indentation N of approximately 0.45 inches.

A children-sized flexible pad has an approximate peak-to-peak distance PP of 1.25 inches at the bottom of the flexible pad 200 tapering to an approximate peak-to-peak distance PP of 1.1 inches at the top of the flexible pad 200 where the notch TT/N is located. In other words, in this particular embodiment, the peak-to-peak distance varies from one end (bottom) of the flexible pad to the other end (top) of the flexible pad. The depth D is approximately 0.15 inches. The height H is approximately 1.4 inches with a notch indentation N of approximately 0.30 inches.

An infant-sized flexible pad has an approximate peak-to-peak distance PP of 0.95 inches at the bottom tapering to an approximate peak-to-peak distance PP of 0.80 inches at the top of the flexible pad 200 where the notch TT/N is located. The depth D is approximately 0.10 inches. The height H is approximately 1.25 inches with a notch indentation N of approximately 0.275 inches.

The flexibility and curvature of the flexible pad 200 allow it to accommodate tendons of varying widths within each subgroup, i.e. infant, children, or adult. The adult-sized flexible pad can accommodate a tendon width as small as approximately 0.79 inches and as great as approximately 1.42 inches.

FIG. 3A shows an adult-sized band assembly 300 that is about 14.5 inches long, exclusive of the VELCRO® hook fastener 102, and about 2.5 inches wide at its widest point. FIG. 3B is a child-sized band assembly 302 that is about 9.75 inches long, exclusive of the VELCRO® hook fastener 102, and about 2.0 inches wide at its widest point. FIG. 3C is an infant-sized band assembly 304 that is about 8.5 inches long, exclusive of the VELCRO® hook fastener 102, and about 1.75 inches wide at its widest point. Besides varying the flexible pad size, the band assembly sizes are varied to allow for a better fit based on the size of a user's limb.

Since the average adult patellar tendon 418 (FIG. 4) is between approximately 0.79 inches and approximately 1.42 inches wide, and the band assembly's peak-to-peak distance PP (FIG. 2B) is approximately 2.2 inches, one can readily calculate a preferable peak-to-peak distance to be approximately double the width of the adult tendon. In other words, the band assembly 100 would have a peak-to-peak distance between approximately 150 percent and approximately 280 percent of the adult tendon width. Similarly, the depth of the valley D (FIG. 2B) would be between approximately 15 percent and approximately 30 percent of the adult tendon width. Corresponding calculations for the child and infant band assemblies show similar ranges for the peak-to-peak distance PP (FIG. 2B) and the valley depth D (FIG. 2B). In other words, irrespective of the subject, the peak-to-peak distance PP (FIG. 2B) for the band assembly 100 would be approximately 150 percent to approximately 280 percent of the tendon width, and the valley depth D (FIG. 2B) would be approximately 15 percent to approximately 30 percent of the tendon width.

Figure 5A:
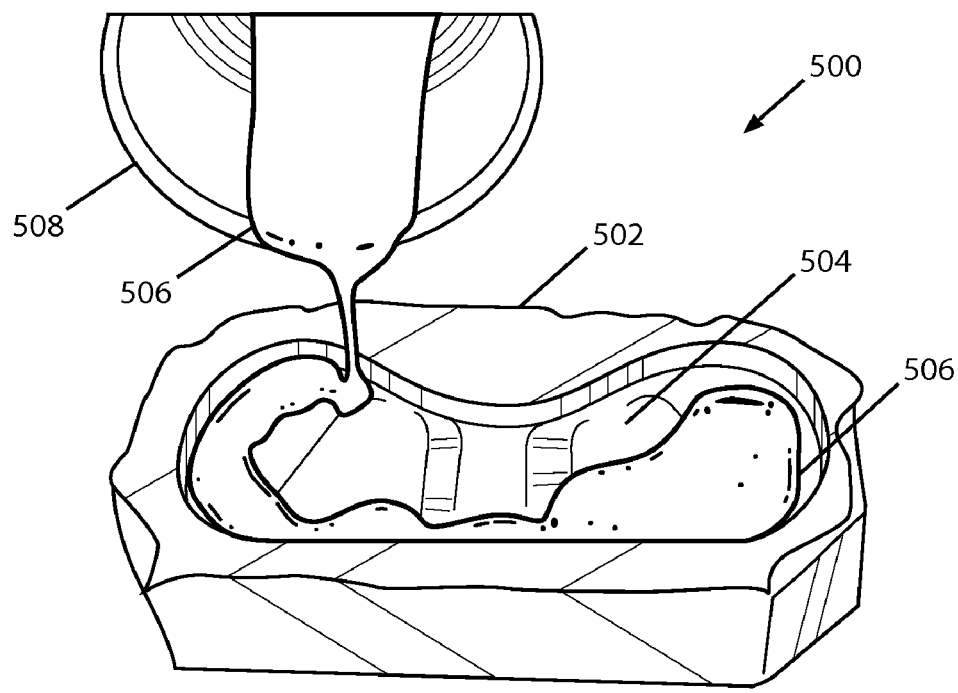
FIG. 5A is a drawing of a mold pouring for the flexible pad.

FIG. 5A shows one embodiment of a pouring process 500 for making the flexible pad 200. A cup 508 is used to pour expanding foam 506 into a mold 502. The contoured cavity 504 of the mold 502 is used to form the rounded surfaces 112b, 116b and valley 114b of the flexible pad 200.

Figure 5B:
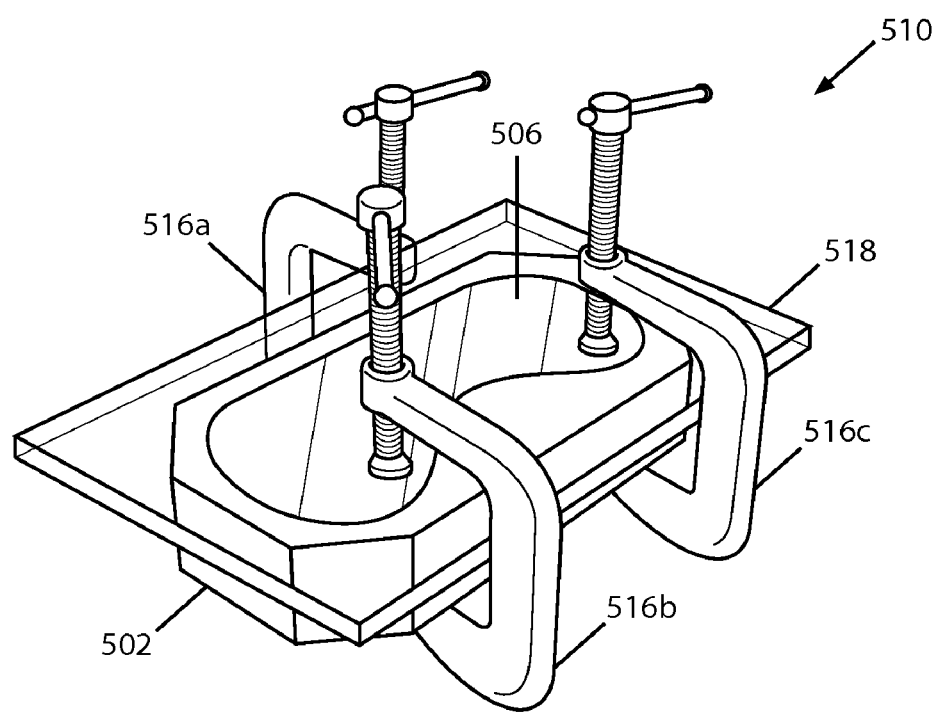
FIG. 5B is a drawing of clamping the mold pouring for the flexible pad.

FIG. 5B shows one embodiment of a setting process 510 for the flexible pad 200. A plastic cover 518 is secured to the mold 502 with clamps 516a, 516b, 516c. The foam 506 expands and is given time to set or become solid. The firmness of the flexible pad 200 is varied by the amount and type of foam 506 that is poured into the mold 502.

Figure 6A:
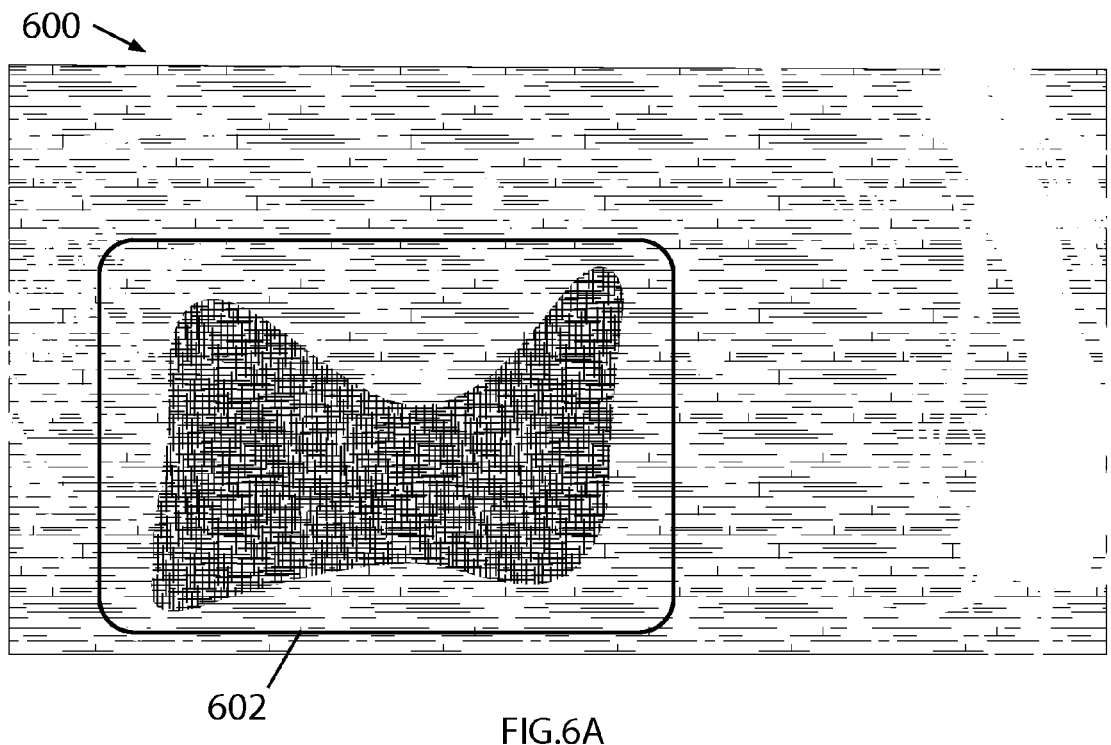
FIG. 6A is a drawing of a film indicating the pressure area of a commercially available knee band.

FIG. 6A shows a pressure-indicating film 600 of a commercially available knee band. The film 600 demonstrates an area 602 of the commercially available knee band that exerts pressure.

Figure 6B:
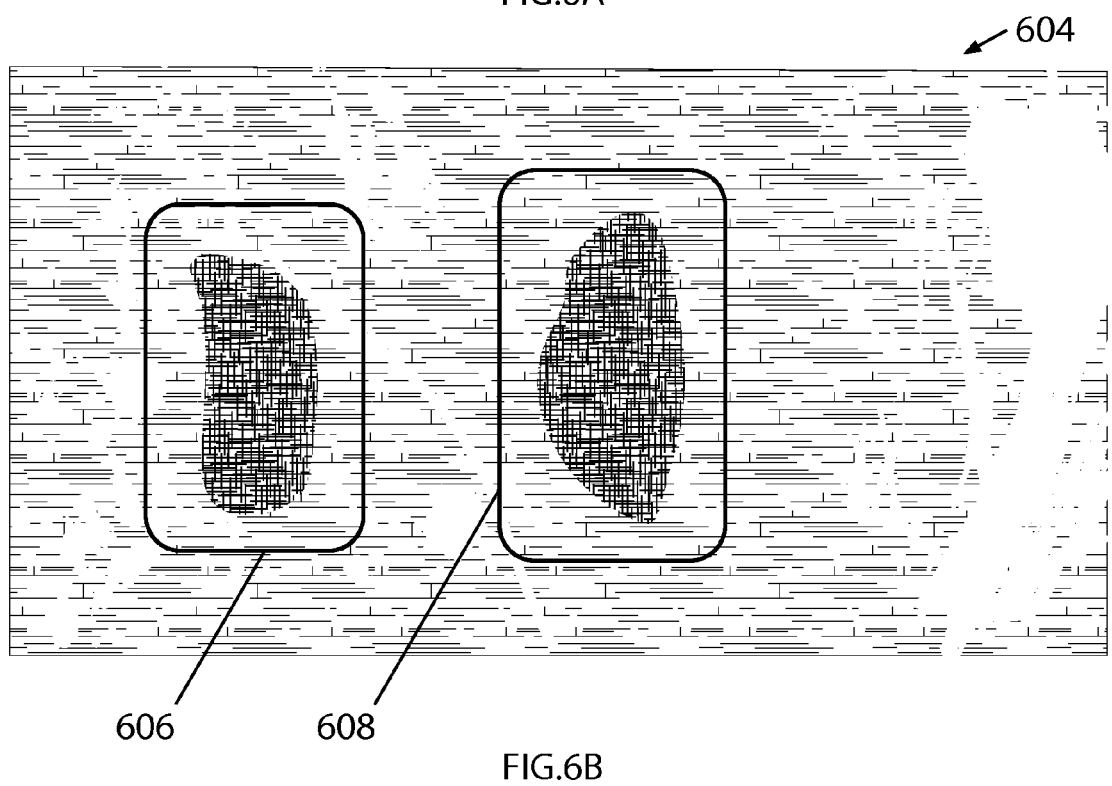
FIG. 6B is a drawing of a film indicating the pressure area of the band assembly.

FIG. 6B shows a pressure-indicating film 604 of the disclosed band assembly 100. The film 604 demonstrates there are two distinct pressure areas 606, 608 exerted by the rounded surfaces 112a, 116a.

Figure 7:
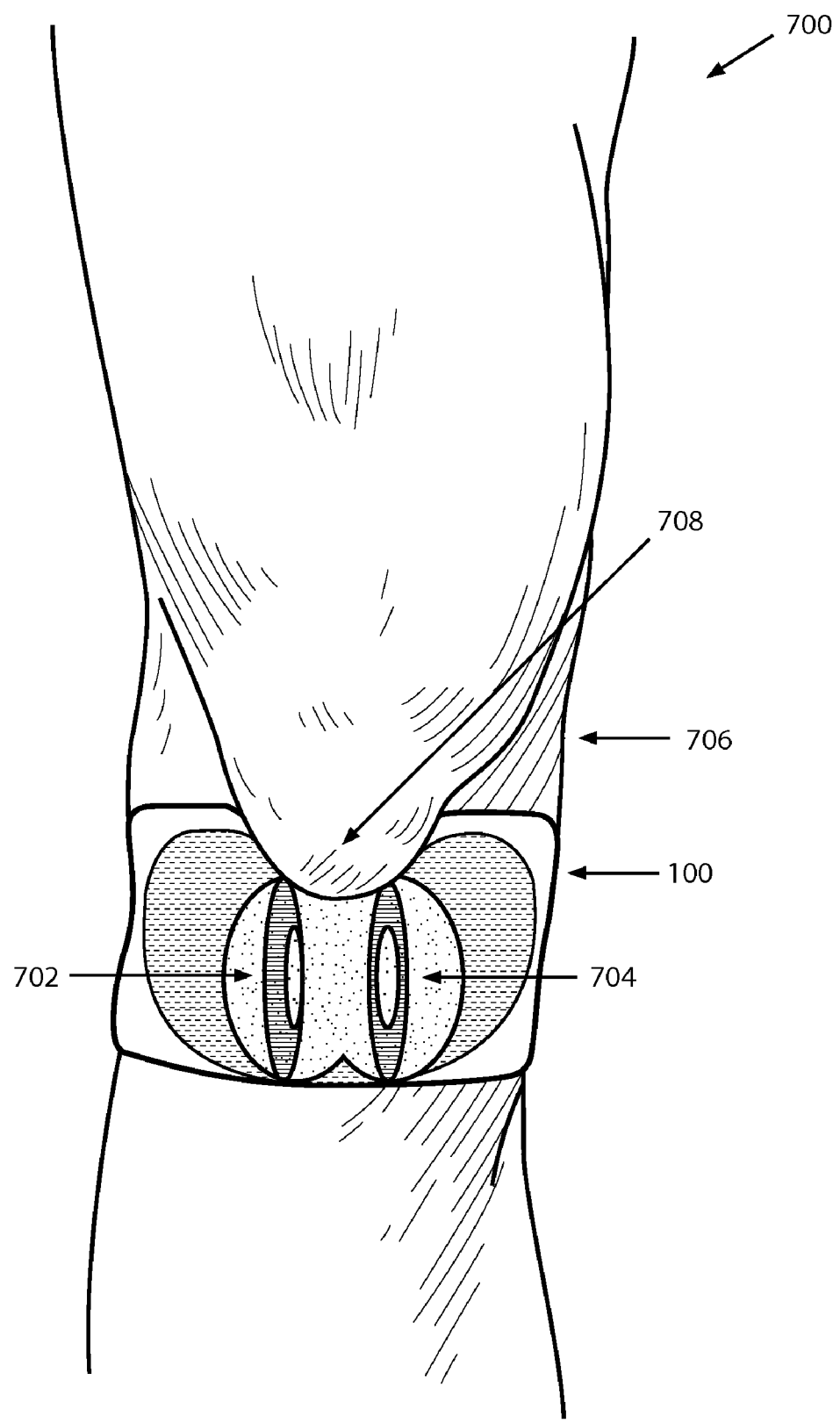
FIG. 7 is a drawing showing the locations where the pressure was measured.

FIG. 7 shows how pressure measurements 700 were taken of the band assembly 100 using force sensor resistors. The band assembly 100 was attached to a leg 706 with the patella 708 substantially centered in the valley 114a between the rounded surfaces 112a, 116a of the flexible pad 200. The resistive left 702 and resistive right 704 measured the pressure applied by the band assembly 100 to the leg 706.

USE AND BENEFITS OF THE INVENTION

When used on a leg, the band assembly 100 is placed directly below and in the center of the knee. The rounded ridges 112a, 116a are in the front of the knee with the notch TT/N (FIG. 2A) between the rounded ridges 112a, 116a facing upward. The notch TT/N (FIG. 2A) aligns with the raised surface on the lower leg bone (tibia) 420 (FIG. 4). The band assembly 100 is secured firmly with the VELCRO® hook fastener 102 and VELCRO® loop fastener 118 but not over tightened so as to constrict important structures surrounding the knee. Pressure from the rounded ridges 112a, 116a is over the proximal, anterior tibia 420 (FIG. 4) with the valley 114a aligned to accommodate the patellar tendon 418 (FIG. 4) in its trajectory to the tibial tubercle.

When used on an arm, the band assembly 100 is placed directly above and in the center of the elbow with the rounded ridges 112a, 116a in the back of the arm. The notch TT/N between the rounded ridges 112a, 116a faces upward and centers between the sides of the elbow joint. The band assembly 100 is secured with the VELCRO® hook fastener 102 and VELCRO® loop fastener 118 so that it will remain in place, but not over-tightened so as to constrict important structures surrounding the elbow. Pressure from the rounded ridges 112a, 116a is over the posterior, distal end of the humerous with the valley 114a aligned to accommodate the triceps tendon.

The band assembly 100 creates improved alignment and function throughout the body by influencing the connective tissue (fascia) and acupressure points on the body. The connective tissue is a continuous web that runs from the top of the head to the tips of the toes and creates the structure of the body. The connective tissue surrounds, cushions, and supports the bones, muscles, organs, nerves, and blood vessels. Outside forces, as well as internal structures, can impact the fascia and create heaviness and immobility.

The band assembly 100 creates a gentle stretch to the connective tissue surrounding the knee through the pocket assembly 106. The rounded surfaces 112a, 116a guide the patellar tendon 418 (FIG. 4) in alignment with the trochlear groove and maintain it there while creating dynamic changes in the alignment of the entire body. These changes can visually be seen when observing a human subject that has properly applied the band assembly 100 to the area surrounding the patellar tendon 418 (FIG. 4). These changes occur from releasing tight connective tissue, as well as from the realigning of acupressure meridians in the body.

Acupressure, developed over 5,000 years ago by the Chinese, uses 365 pressure points on the skin to stimulate the release of tension in the body and to stimulate the body's natural self-curative abilities. The multiple points, which run along meridian channels, many which run from head to foot, connect to specific organs. All the meridians pass through either the knee or the elbow. Placing the pocket assembly 106 below and in front of the knee can affect the arm meridians and placing the pocket assembly 106 on the back of the arm, above the elbow, can affect the leg meridians. Pressure through acupressure points around the knee or elbow releases tension in the connective tissue and allows for improved alignment throughout the body, while also improving symptoms from organ dysfunction.

The rounded surfaces 112a, 116a and valley 114a track the patellar or triceps tendon. The rounded surfaces 112a, 116a disperse pressure through the knee or elbow joint, affecting many acupressure points and creating connective tissue releases. These releases improve alignment and function of the body and reduce pain. The valley 114a on the flexible pad 200 helps to maintain the patellar or triceps tendon in its correct alignment for improved muscle and joint function. As stated before, the flexible pad 200 is made in three sizes, infant, child, and adult, to be used in the corresponding band assembly FIGS. 3A-3C.

Placement of the band assembly 100 on the knee or elbow produces an almost immediate change in alignment throughout the body. Placement of the band assembly 100 below the knee causes the patella 406 (FIG. 4) to move to a more midline position, which reduces knee recurvatum (back knee), knee valgus (knock knee), and knee varum (bowed legs). The patella 406 (FIG. 4) shows improved stability with a more balanced inward and outward movement. The patella 406 (FIG. 4), if in a rotated position, will often correct to a more upright position. With the shifting of the patella 406 (FIG. 4), the talo-calcaneal joint in the foot unlocks and improvements are noted in foot pronation (flat footed) or supination (high arches); the foot moves to a more normal arch position. Toe clawing can decrease, as can forefoot abduction (pulled outward) and adduction (pulled inward). The pelvis, if rotated, will de-rotate, and the anterior iliac spines of the pelvis will become more level. As the pelvis aligns towards a more balanced and equal appearing position, the low back will release tension, as will the rest of the back. Improvements have been noted in scoliosis (lateral curvature of the spine), lordosis (low back arch), and kyphosis (rounded shoulders). The shoulders are noted to become more level with a lengthening of tight neck musculature. The sphenoid bone is a butterfly shaped bone located between the two ears in the skull. Through openings in the bone, the 12 sets of cranial nerves exit. The cranial nerves control the function of the senses, and the organs of the body. They control muscle tone, brain alertness, facial expressions, speech, sucking, and swallowing. When the sphenoid bone is level and aligned, the cranial nerves have improved function. One change almost immediately noted in cranial nerve function with the band assembly 100 is improved eye teaming and eye tracking. All of these results surprisingly-marked improvements are achieved with the band assembly 100 due to the differences between the geometry, flexibility, and topography of prior art devices. Thus, while the differences in geometry, flexibility, and topography of the inventive band assembly 100 may seem small, these differences result in unexpectedly vast improvements when compared to currently-available prior-art devices.

Placement of the band assembly 100 above the elbow demonstrates improved range of motion of the shoulder, neck, and scapula. Through acupressure points and connective tissue releases, individuals with tennis elbow, frozen shoulders, rotator cuff tears, and torticollis can experience more freedom of motion and reduced pain. Similar to significant improvements seen by using the band assembly 100 on the patellar tendon 418 (FIG. 4), marked and unexpectedly-good results are produced from the proper application of the band assembly 100 to the elbow area.

Placement of the band assembly 100 on the arm(s) and leg(s) of children with cerebral palsy decreases flexion (bent) holding patterns and allows for better arm and leg extension for improved walking and arm and hand use. It can decrease ataxic (uncoordinated) movements by stabilizing the knee and elbow joints. For individuals with low muscle tone, placement of the band assembly 100 improves muscle tone through improved midline (centering), improved function of the cranial nerves, and reticular activating system (wakes up the brain). Positive changes in respiration have been noted, with a reduction in stridor (labored) breathing, in a child with severe scoliosis and neuromuscular high tone. All of these effects on the human body have been achieved by properly selecting the right geometry, firmness, and topography of the band assembly 100.

It should be noted that not all of these physical phenomena manifested themselves in all of the patients. Rather, different permutations of these phenomena displayed themselves in different patients. However, it is noteworthy that the inventive band assembly 100 produced results that were superior to other, currently-available products.

Although exemplary embodiments have been shown and described, it will be clear to those of ordinary skill in the art that a number of changes, modifications, or alterations to the disclosure as described may be made. For example, a different material may be substituted for neoprene in the manufacture of the flexible band 126. Also, cotton could be substituted for polyester with spandex in the manufacture of the liner 104.

What is claimed is:

1. A band assembly for aligning a patellar tendon with a trochlear groove, the patellar tendon having a tendon width, the band assembly comprising:
    a flexible strap made of neoprene;
    a liner attached to the flexible strap;
    a flexible pad made of expanding foam, the flexible pad having a length, the flexible pad residing between the flexible strap and the liner;
    a reinforcement strip attached to the flexible strap, the reinforcement strip running the length of the flexible pad;
    a hook fastener attached to one end of the flexible strap;
    a loop fastener attached to an opposing end of the flexible strap;
    elastic edging bordering the flexible strap;
    a first rounded ridge located on the flexible pad, the first rounded ridge having a first peak, the first rounded ridge being configured to apply a first distribution of pressure to a soft-tissue area on a left side of the patellar tendon; and
    a second rounded ridge located on the flexible pad, the second rounded ridge having a second peak, the second peak being separated from the first peak by a peak-to-peak distance, the peak-to-peak distance being approximately double the tendon width, the second rounded ridge being configured to apply a second distribution of pressure on a soft-tissue area on a right side of the patellar tendon, the application of the first distribution of pressure and the second distribution of pressure resulting in alignment of the patellar tendon with the trochlear groove.

* * * * *